(12) United States Patent
Brown et al.

(10) Patent No.: US 11,351,285 B2
(45) Date of Patent: Jun. 7, 2022

(54) REMOVAL OF ORGANIC CONTAMINATION BY OZONE OXIDATION FOR ENVIRONMENTAL SENSOR INTEGRATION

(71) Applicant: Apple Inc., Cupertino, CA (US)

(72) Inventors: Michael K. Brown, Sunnyvale, CA (US); Ashwin Balasubramanian, Sunnyvale, CA (US); Miaolei Yan, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 225 days.

(21) Appl. No.: 16/258,432

(22) Filed: Jan. 25, 2019

(65) Prior Publication Data

US 2020/0237947 A1 Jul. 30, 2020

(51) Int. Cl.
| | |
|---|---|
| *A61L 9/03* | (2006.01) |
| *A61L 9/015* | (2006.01) |
| *A61L 9/20* | (2006.01) |
| *A61L 2/10* | (2006.01) |

(52) U.S. Cl.
CPC ............. *A61L 9/03* (2013.01); *A61L 2202/11* (2013.01); *A61L 2202/12* (2013.01); *A61L 2202/14* (2013.01); *A61L 2202/16* (2013.01); *A61L 2202/20* (2013.01)

(58) Field of Classification Search
CPC ... A61L 9/03; A61L 9/015; A61L 9/20; A61L 2/10
See application file for complete search history.

(56) References Cited

U.S. PATENT DOCUMENTS

| | | | | |
|---|---|---|---|---|
| 6,447,731 | B1* | 9/2002 | Sun | A61L 9/015 422/121 |
| 8,980,188 | B2* | 3/2015 | Park | F25D 17/042 422/186 |
| 2009/0001019 | A1* | 1/2009 | Frometa | B01D 69/02 210/637 |
| 2015/0125355 | A1* | 5/2015 | Lee | B01D 53/007 422/186.3 |
| 2016/0000953 | A1* | 1/2016 | Bettles | A61L 2/24 250/455.11 |
| 2018/0207307 | A1* | 7/2018 | Schwartz | A61L 2/202 |
| 2018/0236121 | A1* | 8/2018 | Worrilow | B01J 20/20 |
| 2020/0086283 | A1* | 3/2020 | Tezuka | B01D 69/10 |

* cited by examiner

*Primary Examiner* — Kevin Joyner
(74) *Attorney, Agent, or Firm* — BakerHostetler (57) ABSTRACT

A portable communication device includes an apparatus for environmental sensing. The apparatus includes a housing, one or more environmental sensors and an ozone source. The housing includes one or more ports for allowing air flow between the surrounding environment and a cavity of the housing. The environmental sensors are coupled to the housing and can sense an environmental agent included in the air flow. The ozone source can generate ozone gas within the cavity of the housing to decompose unwanted organic compounds inside the port.

20 Claims, 5 Drawing Sheets

REMOVAL OF ORGANIC CONTAMINATION BY OZONE OXIDATION FOR ENVIRONMENTAL SENSOR INTEGRATION

TECHNICAL FIELD

The present description relates generally to sensor technology, and more particularly to removal of organic contamination by ozone oxidation for environmental sensor integration.

BACKGROUND

Many mobile electronic devices are equipped with sensors and transducers that enable the devices to perform far more functionalities than communications. Media playing, photography, location detection, online shopping, social media, online banking, calendar and health applications such as heartbeat, blood pressure and blood oxygen level measurement are among the numerous applications that a smart mobile communication device can facilitate. Further, smart mobile communication devices (e.g., smartphones and smartwatches) can be equipped with environmental sensors, such as pressure sensors, humidity sensors and gas sensors.

Environmental sensors integrated into a mobile electronic device can offer novel features such as personal environmental detection and air quality monitoring. However, these devices are prone to organic residue accumulation, such as skin oils, dirt, body hair, etc. Such accumulations can contaminate the device housing and/or the sensor packaging that can produce interference signals and result in increasing sensor errors over an extended period. For example, miniature gas sensors rely on gas diffusion into the device housing to detect an ambient gas and to infer the ambient gas concentration. However, human skin lipids produce squalene, an oily organic compound that can stick to the housing surface and/or sensor packaging. Squalene reacts strongly with oxidizing gases (e.g., ozone and nitrogen oxides), which could significantly increase the errors of such sensors. Conventional methods may use a physical mesh (e.g., a stainless steel mesh) to prevent accumulation of dust or larger particles. The mesh, however, may not be effective against oily organic compounds such as skin oil. Another mitigation scheme adopts active air flow (e.g., by using a pump or a fan) to compensate for analyte depletion. This scheme may not be ideal for mobile devices, given the size, power and noise impacts. Thus, methods suitable for mobile electronic devices are needed to remove organic contaminants and to clean the device housing and sensor packaging in order to ensure accuracy of the environmental sensors.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block-diagram form in order to avoid obscuring the concepts of the subject technology.

In one or more aspects, the subject technology is directed to systems and methods to decompose organic contaminants inside product housing or near sensor packaging, in order to restore the clean environment needed for accurate readings of the integrated environmental sensors. In some implementations, the subject technology decomposes the organic contaminants by using ultraviolet (UV) light to illuminate the contaminants. The disclosed approach can be applied to a number of device platforms, including mobile communication devices such as smartphones and/or smartwatches or other wearable devices hosting environmental sensors. The environmental sensors can include miniature gas sensors such as sensors for volatile organic compounds (VOCs), ozone ($O_3$), nitrogen oxides (NOx), sulfur dioxide ($SO_2$), carbon monoxide (CO) and other environmental gases. A miniature sensor is understood to have dimensions smaller than a few millimeters and can be readily integrated into a smartphone or a smartwatch. The environmental sensors may also include relative humidity (RH) sensors and waterproof pressure sensors.

The disclosed solution can target the self-cleaning of both the interior surface of the device housing or mesh (e.g., aluminum, stainless steel and the waterproof, air-permeable membranes made of materials such as expanded polytetrafluoroethylene (ePTFE) for individual sensors. In some implementations, the process of organic decomposition is based on ozone oxidation of organic compound molecules. The ozone gas can be generated by an ozone source, such as a UV light-emitting diode (LED) or other UV sources, as discussed herein.

In some implementations, the UV LED can be packaged behind the waterproof, air-permeable membrane inside the sensor package, as explained herein. In other implementations, the port geometry can be optimized in order to reduce stray light leakage outside the housing, for example, by using light traps or light baffles.

In one or more aspects of the subject technology, a portable communication device includes an apparatus for environmental sensing. The apparatus includes a housing, one or more environmental sensors and an ozone source. The housing includes one or more ports for allowing air flow between the surrounding environment and a cavity of the housing. The environmental sensors are coupled to the housing and can sense an environmental agent included in the air flow. The ozone source can generate ozone gas within the cavity of the housing to decompose unwanted organic compounds inside the port.

In one or more aspects of the subject technology, a portable communication device includes an apparatus for environmental sensing that includes a housing, one or more environmental sensors and an ozone source. The housing includes a port that allows an air flow to a cavity of the housing. The environmental sensors are coupled to the housing and can sense an environmental agent entering into the housing through a port of the housing. The ozone source generates ozone gas within the cavity of the housing to decompose unwanted organic compounds. The ozone source and the one or more environmental sensors are packaged behind a membrane to reduce a footprint of the apparatus for environmental sensing.

In yet other aspects of the subject technology, an environmental sensing apparatus includes one or more environmental sensors coupled to a housing and capable of sensing an environmental agent in a cavity of the housing. An ozone source generates ozone gas to decompose unwanted organic compounds by oxidation and to prevent the one or more environmental sensors from being contaminated by the unwanted organic compounds. In some implementations, the environmental sensors include an integrated total volatile-organic compound (tVOC) sensor that can monitor completion of the oxidation process.

Figure 1:
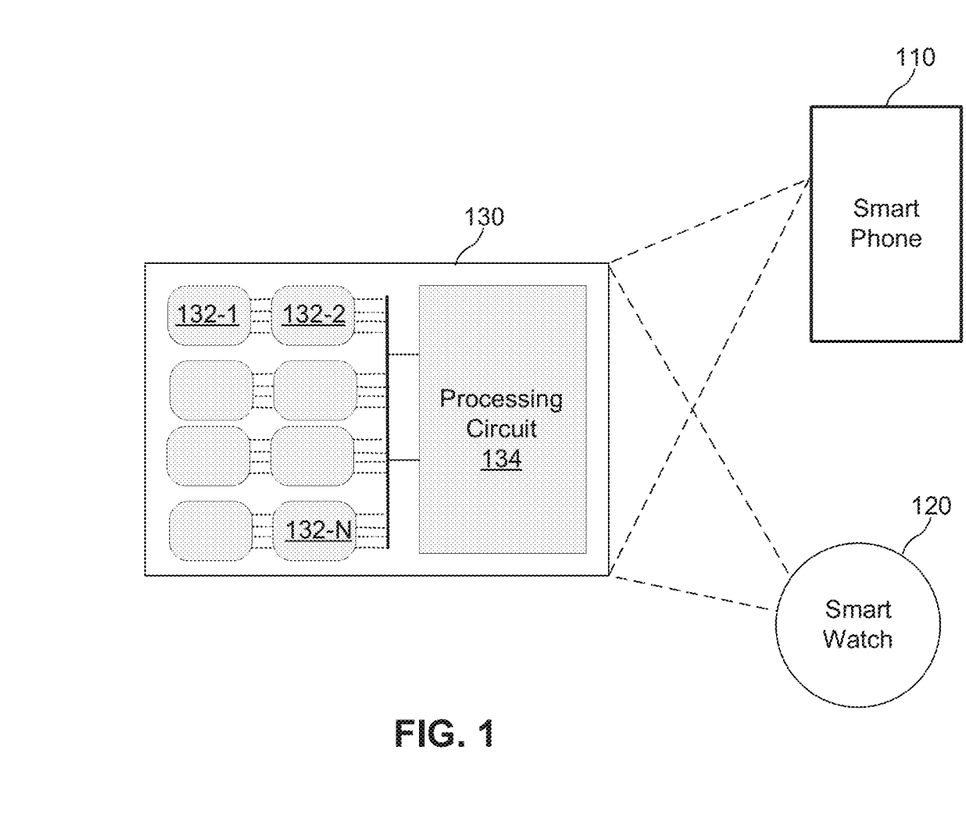
FIG. 1 is a high-level diagram illustrating examples of portable communication devices with environmental sensing capability, in accordance with one or more aspects of the subject technology.

FIG. 1 is a high-level diagram illustrating examples of portable communication devices with environmental sensing capability, in accordance with one or more aspects of the subject technology. The environmental sensing capability of the subject technology can be integrated with a portable communication device such as a smartphone 110 or a smartwatch 120 to enable smartphone 110 or smartwatch 120 to sense environmental gases, for example, to recognize odors (smells) associated with various substances. Smartphone 110 and smartwatch 120 can communicate with other devices by using one or more communication protocols such as Wi-Fi, cellular, Bluetooth, near-filed communication (NFC) and/or other communication protocols. The integration of the environmental sensing capability can make the portable communication device a platform with the capability of running an entire new dimension of applications, for instance, in health, safety, security, networking and other areas.

The portable communication device of the subject technology (e.g., the smartphone 110 or the smartwatch 120) includes an environmental-sensing chip 130 (hereinafter "chip 130") that can communicate with other components of the portable communication device such as a central processor and memory (e.g., no-volatile or volatile memory) of the portable communication device. Chip 130 may include a number of environmental sensors 132 (e.g., patches 132-1, 132-2 ... 132-N) and a processing circuit 134. Chip 130 can be a semiconductor chip such as a silicon chip or a chip made of other semiconductor materials.

Environmental sensors 132 can be gas sensors that can detect many environmental gases, including gases associated with chemical compounds or species that have aroma, odor or flavor. Each environmental sensor 132 is connected to a pair of electrodes. In some implementations, some parameters such as an electrode potential, a DC resistance, an AC impedance or other parameters of environmental sensors 132 can be changed as a result of being exposed to an environmental agent such as VOCs, $O_3$, $NO_x$, $SO_x$, CO, or humidity. The electrodes are continuously monitored and the measured parameters are reported to a central processing unit (CPU) of the portable communication device. In some implementations, the environmental sensor 132 can monitor a reaction product of the photo-oxidation process, including VOCs and can determine a completion of a contamination removal process.

In some implementations, processing circuit 134 integrated on chip 130 and interfaced with environmental sensors 132 can provide biasing for and process the output signal from environmental sensors 132, as described in more detail herein. In one or more implementations, chip 130 may include a large number (e.g., 100-200) of environmental sensors 132 (e.g., patches) and may occupy an area of about 5 mm×5 mm or smaller.

Figure 2:
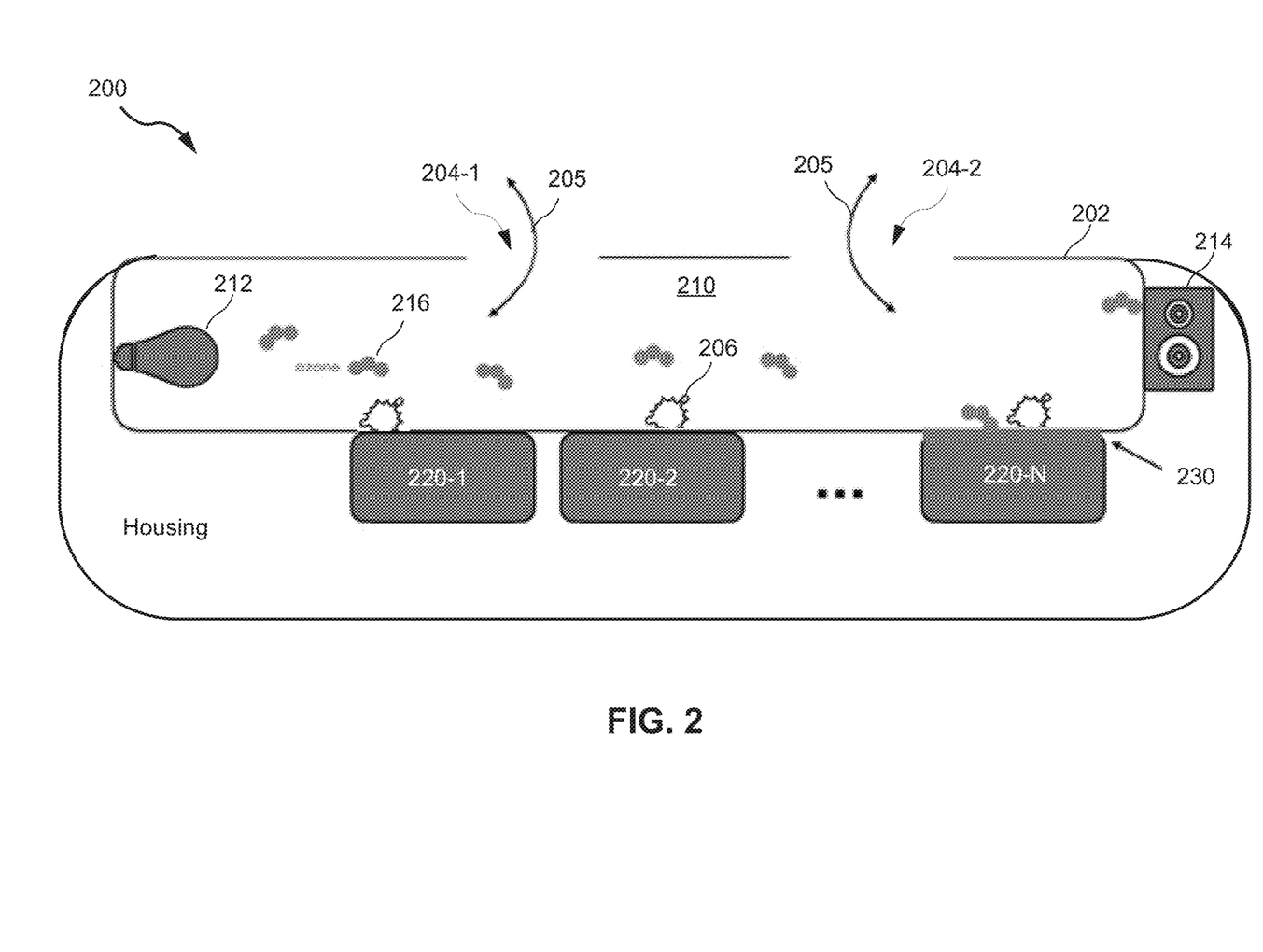
FIG. 2 is a diagram illustrating an example apparatus having an ozone ($O_3$) source for removal of organic contamination, in accordance with one or more aspects of the subject technology.

FIG. 2 is a diagram illustrating an example apparatus 200 having an ozone source for removal of organic contamination, in accordance with one or more aspects of the subject technology. The apparatus 200 includes a housing 202, an ozone source 212 and a number of environmental sensors (hereinafter "sensors") 220 (e.g., 220-1, 220-2 ... 220-N). Housing 202 has a cavity 210 and includes one or more ports 204 (e.g., 204-1 and 204-2). The ports 204 allow a flow of ambient air 205 from (into) the environment around the apparatus 200 into (from) cavity 210. In one or more implementations, one or more of the ports 204 can include a mesh such as a stainless steel mesh to block large particles from entering cavity 210. In some implementations, ports 204 may include a filter for removing particulate matters. In one or more implementations, apparatus 200 includes an air-displacing device 214 such as a micro-speaker that can drive an active airflow in the cavity 210.

In some implementations, sensors 220 can be miniature sensors with dimensions of a few millimeters. Sensors 220 can be sensitive to environmental agents such as various environmental gases 206. For example, sensors 220 can be miniature gas sensors such as sensors for VOCs, $O_3$, $NO_x$, $SO_x$, CO, humidity and other environmental gases. One or more of sensors 220 can be interfaced (e.g., coupled) to housing 202 via a membrane 230. In some implementations, membrane 230 can be air permeable and/or waterproof. In one or more implementations, membrane 230 can be of ePTFE or other material with similar characteristics.

As explained above, environmental sensors may be prone to organic residue accumulation, such as skin oils, dirt, body hair, etc. Such accumulations can contaminate the device housing and/or the sensor packaging, which can produce interference signals and result in increasing sensor errors over an extended period. For example, human skin lipids produce squalene, an oily organic compound that can stick to the housing surface and/or sensor packaging. The subject technology provides solutions that can effectively prevent such contaminations, for example, by using ozone gas 216 to oxidize molecules of the contaminants that results in decomposition of the contaminants such as unwanted organic compounds, for example, squalene, and protect sensors from being contaminated. This can restore the clean environment inside cavity 210 that allows accurate readings of sensors 220.

In some implementations, ozone source 212 can be a UV light source such as a UV LED that can emit UV light with a wavelength within a range of about 180-190 nm, for example, 185 nm. In some implementations, the ozone source (e.g., UV LED) can be driven in a continuous mode or a duty-cycle mode, or during a period of low interest in measurement (e.g., overnight, or device turned off by the user). The duty-cycle mode may include a periodic duty cycle (e.g., ranging from minutes to weeks) or may be based on a battery-charge state of the host device (e.g., a smartphone or smartwatch). For example, when the charge level of the battery of the host device is low, a short duty cycle may be applied.

In one or more implementations, the ozone source can be a mercury-vapor lamp, a low-pass filtered deuterium plasma source, or a corona discharge source, although the UV LED may be more suitable for miniature sensor applications such as in portable communication devices such as smartphones or smartwatches. In some implementations, one of the sensors 220 may be an ozone sensor that can measure a rate of decay of the generated ozone gas 216 to infer the level of remaining contamination within the cavity 210. In one or more implementations, one of the sensors 220 may be a tVOC sensor that can monitor VOCs producing organic materials. As the organic materials are oxidized by ozone gas 216, the level of VOCs detected can reach an equilibrium state when the oxidation source (e.g., ozone source 212) is turned on or off.

Figure 3:
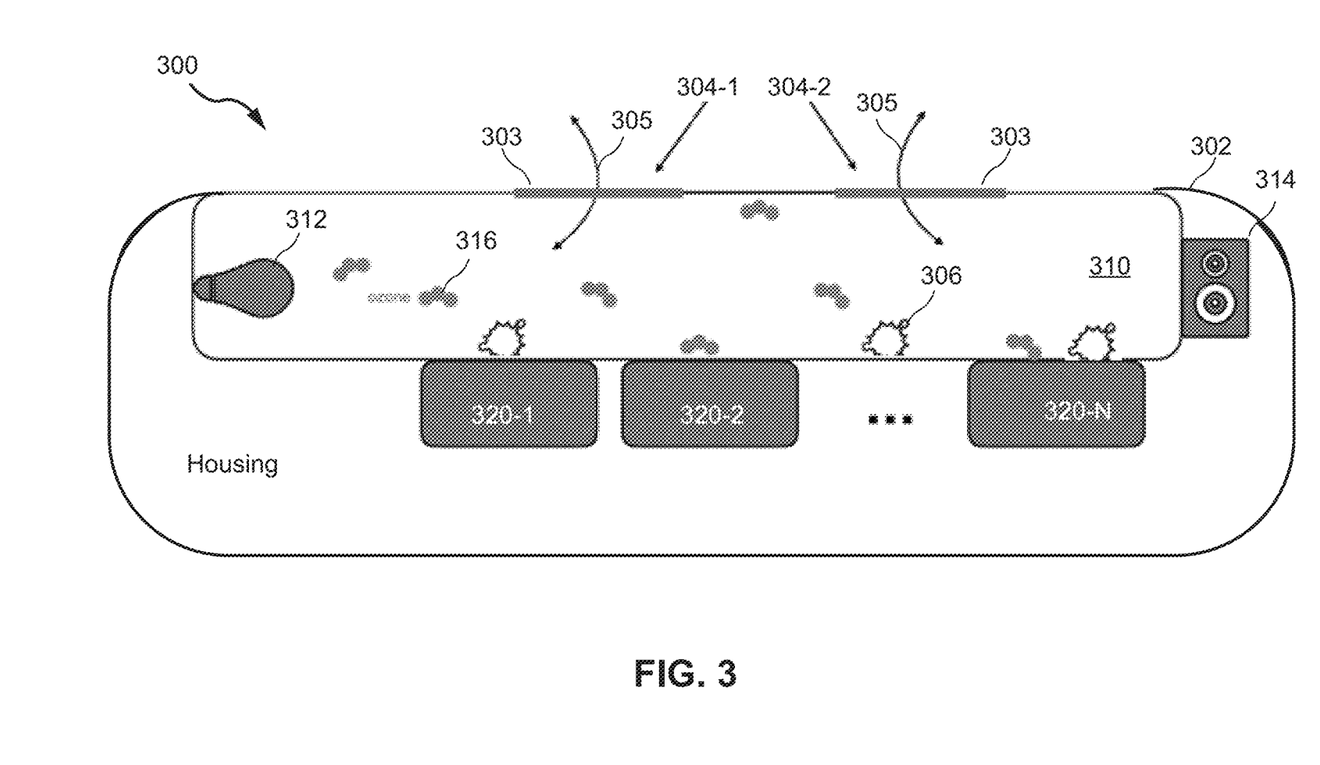
FIG. 3 is a diagram illustrating an example apparatus having a waterproof membrane and an ozone source for removal of organic contamination, in accordance with one or more aspects of the subject technology.

FIG. 3 is a diagram illustrating an example apparatus 300 having a waterproof membrane and an ozone source for removal of organic contamination, in accordance with one or more aspects of the subject technology. Apparatus 300 includes a housing 302, an ozone source 312 and a number of environmental sensors (hereinafter "sensors") 320 (e.g., 320-1, 320-2 . . . 320-N). Housing 302 has a cavity 310 and one or more ports 304 (e.g., 304-1 and 304-2). Port 304 can facilitate a flow (e.g., in-and-out flow) of ambient air 305 from (into) the environment around the apparatus 300 into (from) cavity 310.

In one or more implementations, as shown in FIG. 3, ports 304 can include membranes 303, such as a waterproof and air-permeable membrane. In some implementations, the air-permeable membrane is made of ePTFE or other material with similar characteristics. In some implementations, the membranes 303 can be combined with a filter or a mesh (e.g., made of a porous nickel alloy such as Inconel with micro-drilled holes or micro-porosities) to further facilitate removing particulate matters. In one or more implementations, apparatus 300 includes an air-displacing device 314 such as a micro-speaker that can drive an active airflow through membranes 303, in addition to the diffusion airflow. The Inconel mesh can be especially beneficial when the apparatus 300 or the host device is not waterproofed, and can improve robustness to environmental aggressors such as salt water, sweat and other corrosive material (as compared to stainless steel mesh).

In some implementations, a pressure sensor and a pressure-generating component can be coupled to membrane 303 to monitor a level of mechanical occlusion of membrane 303 by measuring a reduction in membrane permeability over time. In one or more implementations, the temperature of membrane 303 is raised to facilitate destruction of organic matter embedded within membrane 303.

In one or more implementations, sensors 320 are miniature sensors (e.g., few mm size) and can be sensitive to environmental agents 306 such as various gases. For example, sensors 320 can be miniature gas sensors such as sensors for VOCs, $O_3$, $NO_x$, $SO_x$, CO, humidity and other environmental gases. One or more of sensors 320 can be interfaced (e.g., coupled) to housing 302 via a membrane (not shown for simplicity), which can be an air-permeable and/or a waterproof membrane, for example, made of ePTFE or other material with similar characteristics.

In one or more implementations, ozone source 312 can be a UV light source such as a UV LED. The UV LED can emit UV light with a wavelength within a range of about 180-190 nm, for example, 185 nm. In some implementations, the ozone source (e.g., UV LED) can be driven in a continuous mode or a duty-cycle mode, or during a period of low interest in measurement (e.g., overnight, or device turned off by the user). The duty-cycle mode may include a periodic duty cycle (e.g., ranging from minutes to weeks) or may be based on a battery-charge state of the host device (e.g., a smartphone or smartwatch). For example, when the charge level of the battery of the host device is low, a short duty cycle may be applied.

In some implementations, ozone source 312 can be a mercury-vapor lamp, a low-pass filtered deuterium plasma source, or a corona discharge source, although the UV LED may be more suitable for miniature sensor applications such as in portable communication devices such as smartphones or smartwatches. In some implementations, one of the sensors 320 may be an ozone sensor that can measure a rate of decay of the generated ozone gas 316 to infer the level of remaining contamination within cavity 310. In one or more implementations, one of the sensors 320 may be a tVOC sensor that can monitor VOCs producing organic materials. As the organic materials are oxidized by ozone gas 316, the level of VOCs detected can reach an equilibrium state when the oxidation source (e.g., ozone source 312) is turned on or off. In one or more implementations, multiple ozone sources can be used to enhance the efficiency of organic contamination removal.

Figure 4:
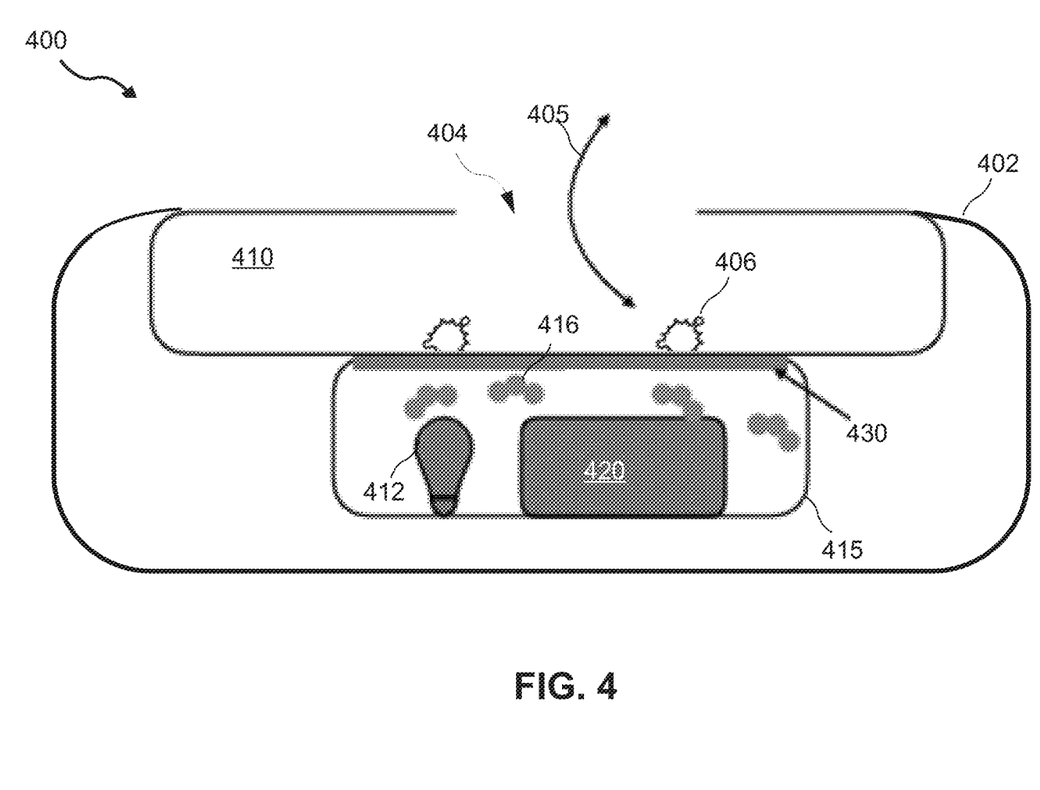
FIG. 4 is a diagram illustrating an example apparatus having an ozone source packaged with the environmental sensor for removal of organic contamination, in accordance with one or more aspects of the subject technology.

FIG. 4 is a diagram illustrating an example apparatus 400 having an ozone source packaged with the environmental sensor for removal of organic contamination, in accordance with one or more aspects of the subject technology. Example apparatus 400 is a compact and low-footprint implementation and includes a housing 402 having a cavity 410 and a sensor package 415. Sensor package 415 is interfaced with housing 402 using a membrane 430, which can be an air-permeable and/or waterproof membrane made of, for example, ePTFE or other material having similar characteristics.

Housing 402 includes a port 404 to allow air flow 405 between cavity 410 and the surrounding environment. Sensor package 415 includes an environmental sensor 420 and an ozone source (e.g., a UV light source) 412 for generating ozone gas 416 to remove (e.g., by oxidizing and decomposing) unwanted organic compounds in order to prevent the unwanted organic compounds from reaching environmental sensor 420. In some implementations, a membrane 430 separates sensor package 415 from cavity 410 of housing 402. In one or more implementations, membrane 430 can be combined with a filter or a mesh (e.g., made of a porous nickel alloy such as Inconel with micro-drilled holes or micro-porosities) to further facilitate removing particulate matters. In one or more implementations, apparatus 400 includes an air-displacing device (not shown for simplicity) such as a micro-speaker that can drive an active airflow through membrane 430, in addition to the diffusion airflow.

In some implementations, a pressure sensor and a pressure-generating component can be coupled to membrane 430 to monitor a level of mechanical occlusion of membrane 430 by measuring a reduction in membrane permeability over time. In one or more implementations, the temperature of membrane 430 is raised to facilitate destruction of organic matter embedded within membrane 430.

In one or more implementations, environmental sensor 420 is a miniature (e.g., few mm in size) environmental sensor that is sensitive to environmental agents 406 such as VOCs, $O_3$, $NO_x$, $SO_x$, CO, or humidity. The integration of ozone source 412 and environmental sensor 420 within sensor package 415 reduces the footprint of apparatus 400 and allows for using the apparatus 400 in more compact consumer electronic devices such as portable communication devices (e.g., smartphones and smartwatches).

In some implementations, ozone source 412 is a UV LED and can be driven in a continuous mode or a duty-cycle mode, or during a period of low interest in measurement (e.g., overnight, or device turned off by the user). The duty-cycle mode may include a periodic duty cycle (e.g., ranging from minutes to weeks) or may be based on a battery-charge state of the host device (e.g., a smartphone or smartwatch). For example, when the charge level of the battery of the host device is low, a short duty cycle may be applied.

Figure 5:
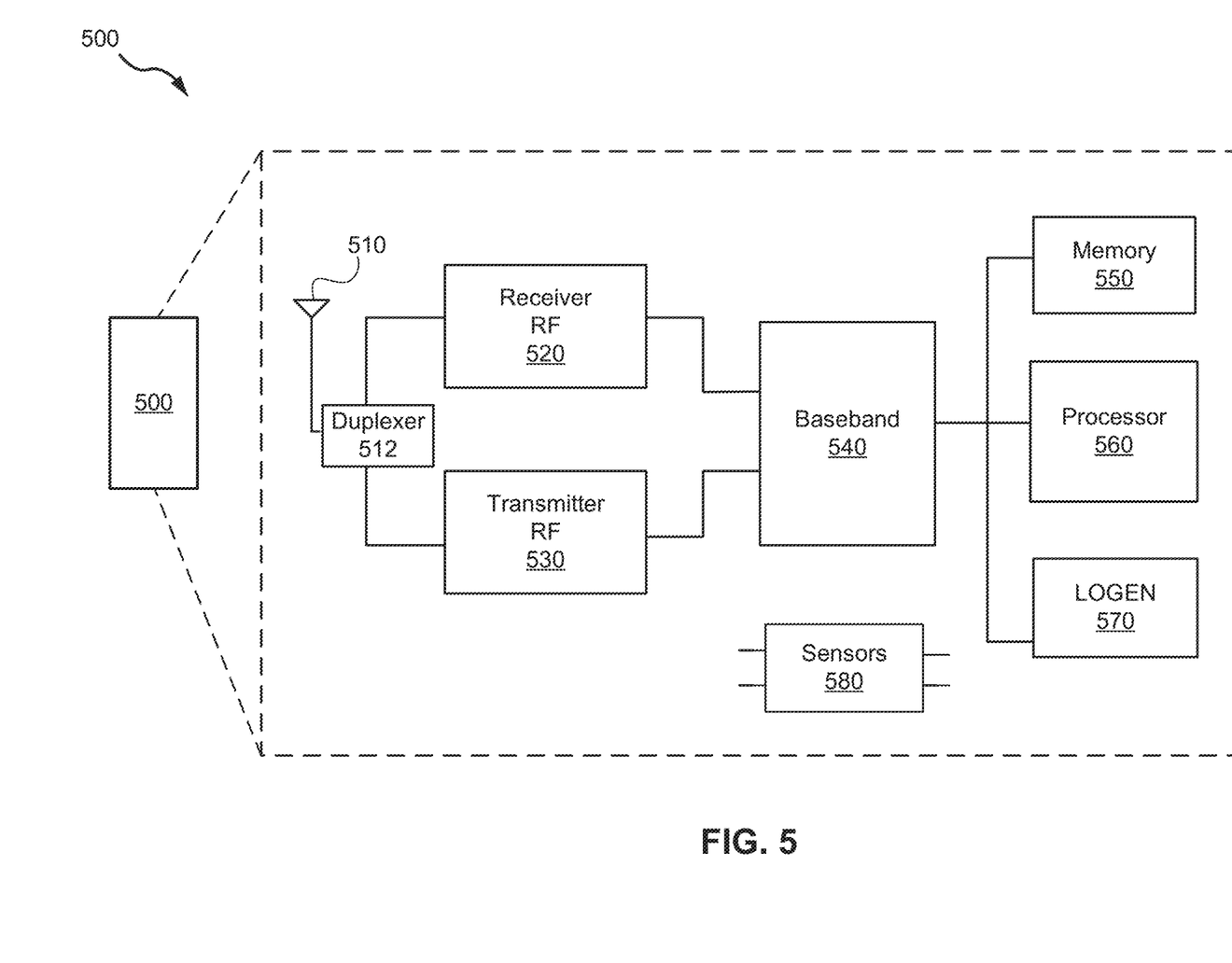
FIG. 5 is a block diagram illustrating an example wireless communication device, within which one or more environmental sensors of the subject technology can be integrated.

FIG. 5 is a block diagram illustrating an example wireless communication device 500, within which one or more environmental sensors of the subject technology can be integrated. The wireless communication device 500 may comprise a radio-frequency (RF) antenna 510, a duplexer 512, a receiver 520, a transmitter 530, a baseband processing module 540, a memory 550, a processor 560, a local oscillator generator (LOGEN) 570 and one or more sensors 580. In various embodiments of the subject technology, one or more of the blocks represented in FIG. 5 may be integrated on one or more semiconductor substrates. For example, the blocks 520-570 may be realized in a single semiconductor chip or a single system on a semiconductor chip, or may be realized in a multi-semiconductor chip semiconductor chipset.

The receiver 520 may comprise suitable logic circuitry and/or code that may be operable to receive and process signals from the RF antenna 510. The receiver 520 may, for example, be operable to amplify and/or down-convert received wireless signals. In various embodiments of the subject technology, the receiver 520 may be operable to cancel noise in received signals and may be linear over a wide range of frequencies. In this manner, the receiver 520 may be suitable for receiving signals in accordance with a variety of wireless standards such as Wi-Fi, WiMAX, Bluetooth, and various cellular standards. In various embodiments of the subject technology, the receiver 520 may not require any surface-acoustic wave (SAW) filters and few or no off-semiconductor chip discrete components such as large capacitors and inductors.

The transmitter 530 may comprise suitable logic circuitry and/or code that may be operable to process and transmit signals from the RF antenna 510. The transmitter 530 may, for example, be operable to up-convert baseband signals to RF signals and amplify RF signals. In various embodiments of the subject technology, the transmitter 530 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 530 may be operable to provide signals for further amplification by one or more power amplifiers.

The duplexer 512 may provide isolation in the transmit band to avoid saturation of the receiver 520 or damaging parts of the receiver 520, and to relax one or more design requirements of the receiver 520. Furthermore, the duplexer 512 may attenuate the noise in the receive band. The duplexer 512 may be operable in multiple frequency bands of various wireless standards.

The baseband processing module 540 may comprise suitable logic, circuitry, interfaces, and/or code that may be operable to perform processing of baseband signals. The baseband processing module 540 may, for example, analyze received signals and generate control and/or feedback signals for configuring various components of the wireless communication device 500, such as the receiver 520. The baseband processing module 540 may be operable to encode, decode, transcode, modulate, demodulate, encrypt, decrypt, scramble, descramble, and/or otherwise process data in accordance with one or more wireless standards.

The processor 560 may comprise suitable logic, circuitry, and/or code that may enable processing data and/or controlling operations of the wireless communication device 500. In this regard, the processor 560 may be enabled to provide control signals to various other portions of the wireless communication device 500. The processor 560 may also control transfers of data between various portions of the wireless communication device 500. Additionally, the processor 560 may enable implementation of an operating system or otherwise execute code to manage operations of the wireless communication device 500.

The memory 550 may comprise suitable logic, circuitry, and/or code that may enable storage of various types of information such as received data, generated data, code, and/or configuration information. The memory 550 may comprise, for example, RAM, ROM, flash, and/or magnetic storage. In various embodiments of the subject technology, information stored in the memory 550 may be utilized for configuring the receiver 520 and/or the baseband processing module 540.

The LOGEN 570 may comprise suitable logic, circuitry, interfaces, and/or code that may be operable to generate one or more oscillating signals of one or more frequencies. The LOGEN 570 may be operable to generate digital and/or analog signals. In this manner, the LOGEN 570 may be operable to generate one or more clock signals and/or sinusoidal signals. Characteristics of the oscillating signals such as the frequency and duty cycle may be determined based on one or more control signals from, for example, the processor 560 and/or the baseband processing module 540.

In operation, the processor 560 may configure the various components of the wireless communication device 500 based on a wireless standard according to which it is desired to receive signals. Wireless signals may be received via the RF antenna 510 and amplified and down-converted by the receiver 520. The baseband processing module 540 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device 500, data to be stored to the memory 550, and/or information affecting and/or enabling operation of the wireless communication device 500. The baseband processing module 540 may modulate, encode, and perform other processing on audio, video, and/or control signals to be transmitted by the transmitter 530 in accordance with various wireless standards.

The one or more sensors 580 may include the sensors 132 of FIG. 1. The sensors 132 of the subject technology can be readily integrated into the wireless communication device 500, in particular when the wireless communication device 500 is a smartphone or a smartwatch. The wireless communication device 500 can benefit from the disclosed removal of organic contamination by using an ozone source, as discussed above with respect to the apparatuses of FIGS. 2-4.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter genders (e.g., her and its) and vice versa. Headings and subheadings, if any, are used for convenience only and do not limit the subject disclosure.

The predicate words "configured to", "operable to" and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A portable communication device, the device comprising:
    an apparatus for environmental sensing comprising:
       a housing including one or more ports for allowing an air flow between a surrounding environment and a cavity of the housing;
       one or more environmental sensors coupled to the housing and configured to sense an environmental agent included in the air flow; and
       an ozone source integrated within the cavity of the housing and configured to generate ozone gas within the cavity of the housing to decompose unwanted organic compounds.

2. The device of claim 1, further comprising an air-permeable membrane between the one or more environmental sensors and the housing.

3. The device of claim 2, wherein the air-permeable membrane comprises a waterproof membrane, wherein the air-permeable membrane comprises expanded polytetrafluoroethylene (ePTFE).

4. The device of claim 1, wherein the ozone source comprises an ultraviolet (UV) source, wherein the UV source comprises a UV light-emitting diode (LED) configured to produce UV light with a wavelength of within a range of about 180-190 nm, and wherein the ozone gas generated by the UV source is configured to decompose the unwanted organic compounds by oxidization of molecules of the unwanted organic compounds.

5. The device of claim 1, wherein the ozone source comprises one of a UV LED, a mercury-vapor lamp, a low-pass filtered deuterium plasma source, or a corona discharge source.

6. The device of claim 1, wherein at least one of the one or more environmental sensors comprises an ozone sensor configured to monitor a rate of decay of the generated ozone gas to infer a level of remaining unwanted organic compounds.

7. The device of claim 1, wherein the ozone source is disposed inside the cavity of the housing, and wherein the ozone source is driven in a continuous mode or a duty-cycle mode, or during a period of low interest in measurement, wherein the duty-cycle mode comprises a periodic duty cycle or is based on a battery-charge state.

8. The device of claim 1, wherein the one or more environmental sensors comprise a miniature gas sensor or a pressure sensor.

9. The device of claim 1, wherein the environmental agent comprises at least one of volatile organic compounds (VOCs), ozone, nitrogen oxides, sulfur oxides, carbon monoxide, or humidity.

10. The device of claim 1, wherein the one or more ports include a membrane, wherein the membrane comprises an air-permeable and waterproof membrane, wherein the waterproof membrane comprises ePTFE, and wherein the membrane is combined with a mesh or a particulate filter.

11. The device of claim 10, further comprising an air-displacing device coupled to the housing to drive an active airflow through the membrane, wherein the air-displacing device comprises a micro-speaker.

12. A portable communication device, the device comprising:
    an apparatus for environmental sensing comprising:
       a housing including a port, wherein the port is configured to allow an air flow to and from a cavity of the housing;
       one or more environmental sensors coupled to the housing and configured to sense an environmental agent entered into the housing; and
       an ozone source integrated with the cavity of the housing and configured to generate ozone gas within the cavity of the housing to decompose unwanted organic compounds, wherein the ozone source and the one or more environmental sensors are packaged behind a membrane of the cavity to reduce a footprint of the apparatus for environmental sensing.

13. The device of claim 12, wherein the membrane comprises a waterproof, air-permeable membrane, wherein the membrane comprises expanded polytetrafluoroethylene (ePTFE).

14. The device of claim 13, wherein a temperature of the membrane is raised to facilitate destruction of organic matter embedded within the waterproof, air-permeable membrane.

15. The device of claim 12, wherein the ozone source comprises an ultra-violet (UV) source, wherein the UV source comprises a UV light-emitting diode (LED) configured to produce UV light with a wavelength of within a range of about 180-190 nm.

16. The device of claim 12, wherein the one or more environmental sensors comprise a miniature gas sensor or a pressure sensor, and the environmental agent comprises at least one of volatile organic compounds (VOCs), ozone, nitrogen oxides, sulfur oxides, carbon monoxides, or humidity.

17. An environmental sensing apparatus, the apparatus comprising:
one or more environmental sensors coupled to a housing and configured to sense an environmental agent in a cavity of the housing;
an ozone source integrated within a cavity of the housing and configured to generate ozone gas to decompose unwanted organic compounds by oxidation and to prevent the one or more environmental sensors from being contaminated by the unwanted organic compounds; and
a pressure sensor and a pressure-generating component coupled to an air-permeable membrane,
wherein the housing includes one or more ports covered by the air-permeable membrane for allowing an air flow between a surrounding environment and the cavity of the housing.

18. The apparatus of claim 17, wherein the housing includes one or more ports, wherein the one or more ports include the air-permeable membrane, wherein the air-permeable membrane comprises a porous nickel alloy, wherein the air-permeable membrane further comprises a particulate matter filter, and wherein the air-permeable membrane comprises a waterproof, air-permeable membrane.

19. The apparatus of claim 17, wherein the pressure sensor and the pressure-generating component are configured to monitor a level of mechanical occlusion of the air-permeable membrane by measuring a reduction in membrane permeability over time.

20. The apparatus of claim 17, wherein the one or more environmental sensors comprise a miniature gas sensor or a pressure sensor, and wherein the one or more environmental sensors further include an integrated total VOC sensor configured to monitor completion of oxidation process.

* * * * *